(12) United States Patent
Baniel et al.

(10) Patent No.: US 7,411,090 B2
(45) Date of Patent: Aug. 12, 2008

(54) PROCESS FOR THE RECOVERY OF CITRIC ACID

(75) Inventors: Avraham Baniel, Jerusalem (IL); Asher Vitner, Jerusalem (IL); David Gonen, Herzeliya Pituach (IL); David Heidel, Decatur, IL (US)

(73) Assignee: A.E. Staley Manufacturing Company, Decatur, IL (US)

( * ) Notice: Subject to any disclaimer, the term of this patent is extended or adjusted under 35 U.S.C. 154(b) by 0 days.

(21) Appl. No.: 10/548,171

(22) PCT Filed: Mar. 3, 2004

(86) PCT No.: PCT/IL2004/000203

§ 371 (c)(1),
(2), (4) Date: Apr. 10, 2006

(87) PCT Pub. No.: WO2004/087631

PCT Pub. Date: Oct. 14, 2004

(65) Prior Publication Data

US 2006/0247468 A1    Nov. 2, 2006

(30) Foreign Application Priority Data

Mar. 31, 2003   (IL) ..................................... 155161

(51) Int. Cl.
*C07C 51/42* (2006.01)
*C07C 55/00* (2006.01)

(52) U.S. Cl. ..................................... 562/593; 562/590

(58) Field of Classification Search ................. 562/584, 562/513
See application file for complete search history.

(56) References Cited

U.S. PATENT DOCUMENTS 5,231,225 A * 7/1993 Baniel et al. ................. 562/513
5,352,825 A * 10/1994 Felman et al. ............... 562/580
5,426,220 A    6/1995 Baniel et al.

FOREIGN PATENT DOCUMENTS

EP    0 432 610    6/1991

* cited by examiner

*Primary Examiner*—Karl J Puttlitz
(74) *Attorney, Agent, or Firm*—Oblon, Spivak, McClelland, Maier & Neustadt, P.C.

(57) ABSTRACT

The invention provides a process for the recovery of citric acid from an aqueous solution feed stream originating in fermentation of carbohydrates and utilizing an amine solvent extraction step for separation of impurities comprising: subjecting said aqueous solution feed stream A to a treatment for partial recovery of citric acid, wherein said treatment is other than amine solvent extraction, to form a first portion of purified citric acid B and a secondary feed stream F; subjecting at least a portion G of said secondary feed stream F to a treatment consisting of amine solvent extraction to form a second portion of purified citric acid solution and to reject substantial of impurities initially present in said portion of said secondary feed stream; subjecting said second portion of purified citric acid solution to crystallization; and recycling mother liquor from said crystallization.

11 Claims, 9 Drawing Sheets

PROCESS FOR THE RECOVERY OF CITRIC ACID

The present invention relates to the recovery of citric acid from aqueous solutions originating in industrial fermentation of carbohydrates. More particularly, the present invention relates to an improved process for the recovery of citric acid from an aqueous solution feed stream originating in fermentation of carbohydrates and utilizing an amine solvent extraction step for separation of impurities.

Amine Extractants are used industrially to recover citric acid from solutions at low concentrations such that are typical of fermentation broths and also at high concentrations obtained generally by pre-concentration of such broths. Generally prior to extraction the filtered fermentation broth is subjected to the removal of cations in order to secure complete extraction of the citric acid as well as other acids present as trace impurities. The latter comprise acids that are stronger than citric acid both mineral ($HCl$, $H_2SO_4$, $H_3PO_4$) and organic (e.g. oxalic) as well as acids weaker than citric acid (e.g. acetic acid). All contaminating acids are separated from citric acid as part of the Amine Extractant recovery by playing on selectivities of the extractant with respect to acid strength. The stronger acids may alternately be removed by pretreatment of the decationised broth by solid anion exchangers. The practice of the present invention assumes as feed filtered decationised broth treated for removal of contaminating acids. This feed is to be referred to as "treated broth". As to the mode of removal of contaminating acids, both of the described modes are compatible with the practice of the present invention, the choice of anion exchange by a liquid or by a solid exchanger is an optional choice for the practitioner of the present invention.

An outstanding quality of Amine Extractants is the efficiency and completeness of separating acids in an aqueous solution from neutral molecules present in the same solution: the acids report to the organic phase whereas the neutral solutes report very weakly if at all. Fermentation broths contain an enormous variety of essentially neutral solutes: residual feed carbohydrates, their transformation products other than citric acid, as well as obligate by-products of the activity of the microorganism effecting the fermentation.

The efficiency of this separation is practically independent of the ratio of impurities to citric acid. Crystallization, which is the other major separation technology in use in citric acid recovery, is very sensitive to this ratio and therefore limited in its applicability. Thus, carefully filtered broths thoroughly treated for maximum impurities removal by cation exchange and anion exchange, when treated for direct recovery of citric acid by crystallization, provide only for some 10% recovery at the required food grade quality, beyond which the purity decreases with the increase in impurities to citric acid ratio. The impurities are mostly neutral solutes as explained above. These solutes in effect block the direct use of crystallization which, when applicable, are economically efficient.

Low molecular weight oxygenated solvents such as alkanols (e.g. n-butanol) and esters (e.g. ethylacetate) can be used to recover pure citric acid from concentrated aqueous solutions separating it from impurities by simple low-cost liquid-liquid extraction operations. This approach which has not been previously proposed (GB874030) is described in detail further below. It is more efficient in recovering pure citric acid from concentrated fermentation broth than crystallization but the efficiency falls with the extent of recovery and the concurrent increase in the ratio of impurities to citric acid.

The present invention provides for novel systems of citric acid recovery amenable to flexible design and having efficiencies not attainable by existing technologies.

Thus according to the present invention there is now provided a process for the recovery of citric acid from an aqueous solution feed stream originating in fermentation of carbohydrates and utilizing an amine solvent extraction step for separation of impurities comprising:

One) subjecting said aqueous solution feed stream A to a treatment for partial recovery of citric acid, wherein said treatment is other than amine solvent extraction, to form a first portion of purified citric acid B and a secondary feed stream F;

Two) subjecting at least a portion G of said secondary feed stream F to a treatment consisting of amine solvent extraction to form a second portion of purified citric acid solution and to reject substantially all of the impurities initially present in said portion of said secondary feed stream.

Three) subjecting said second portion of purified citric acid solution to crystallization; and Four) recycling mother liquor from said crystallization.

In further preferred embodiments of the present invention the treatment step of step a) is a multi-step treatment.

Thus, in a first preferred embodiment of the present invention the initial secondary feed stream formed in a), prior to being sent to amine solvent extraction, is subjected to a second step of partial citric acid recovery and this second portion of citric acid bypasses b) to join the purified citric acid solution produced in b) that feeds crystallization c).

Thus in said preferred embodiments of the present invention the initial secondary feed stream formed in step a, prior to being sent to said treatment of amine solvent extraction, is subjected to a second step of partial citric acid recovery to form a partially purified citric acid and a tertiary feed stream wherein tertiary feed stream is subjected to a treatment of amine solvent extraction according to step b and said partially purified citric acid bypasses step b and is directly subjected to crystallization treatment together with the purified citric acid solution produced in step b.

In especially preferred embodiments of the present invention said aqueous solution feed stream A contains citric acid at a concentration of between 16% and 75%.

In first preferred embodiments of the present invention said secondary feed stream F contains citric acid at a concentration of about 5% to 30% while in other preferred embodiments of the present invention said secondary feed stream F contains citric acid at a concentration of about 16% to 75%.

The technologies made possible by the present invention are described in relation to citric acid fermentations fed by carbohydrates low in impurities levels which results in fermentation broths in which the impurities that accompany the citric acid that is formed are mostly neutral and of minor amounts compared to the citric acid content of the broth. Such broths are amenable to recovery by Solvent Extraction (hereinafter referred to as SX) applying amine extractants—as practiced on large industrial scale. However the invention is not restricted to this particular source of citric acid. Any primary citric acid aqueous solution amenable to recovery by an Amine Extractant (hereinafter referred to as an AE) can benefit by the present invention. Thus for instance, a fermentation broth derived from impurities-rich molasses can be treated by the traditional lime/sulfuric process to obtain a citric acid solution amenable to AE-recovery and to the benefits of the present invention.

While the invention will now be described in connection with certain preferred embodiments in the following examples and with reference to the accompanying figures, so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to the most useful and readily understood description of the principles and conceptual aspects of the invention.

In the drawings:

FIG. 6 is a schematic flow sheet representation of a preferred process as described in Example 4 hereinafter; and.

Figure 1:
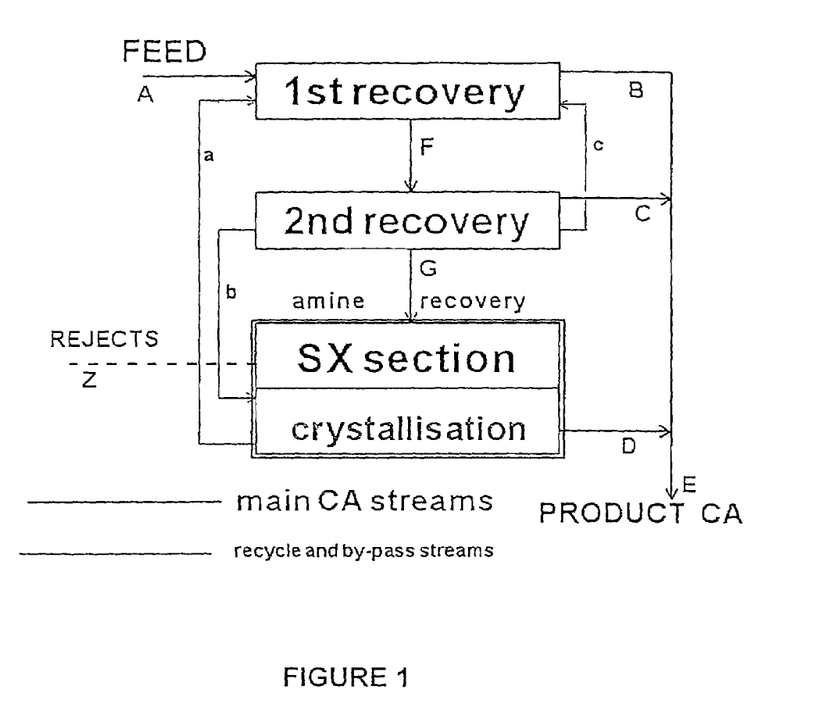
FIG. 1 is a schematic flow sheet representation of the concept of the present invention.

The concept underlying the invention is now explained in conjunction with the diagram in FIG. 1. Letters in [] refer to stream designations in FIG. 1

One) The core of each overall recovery system consists of a unit of two sections: (1) a Solvent Extraction (SX) by Amine Extractant section which recovers practically fully all citric acid fed to it and rejects practically all the impurities that accompany this citric acid as in present art and (2) a crystallization section that accepts the purified aqueous citric acid from the SX unit (as in present art) as well as citric acid streams originating in treatments of the primary feed preceding amine solvent recovery and that bypass amine extraction to feed directly into the crystallization section. This core amine recovery section of the overall recovery system is presented in greater detail in FIG. 1a.

Figure 1A:
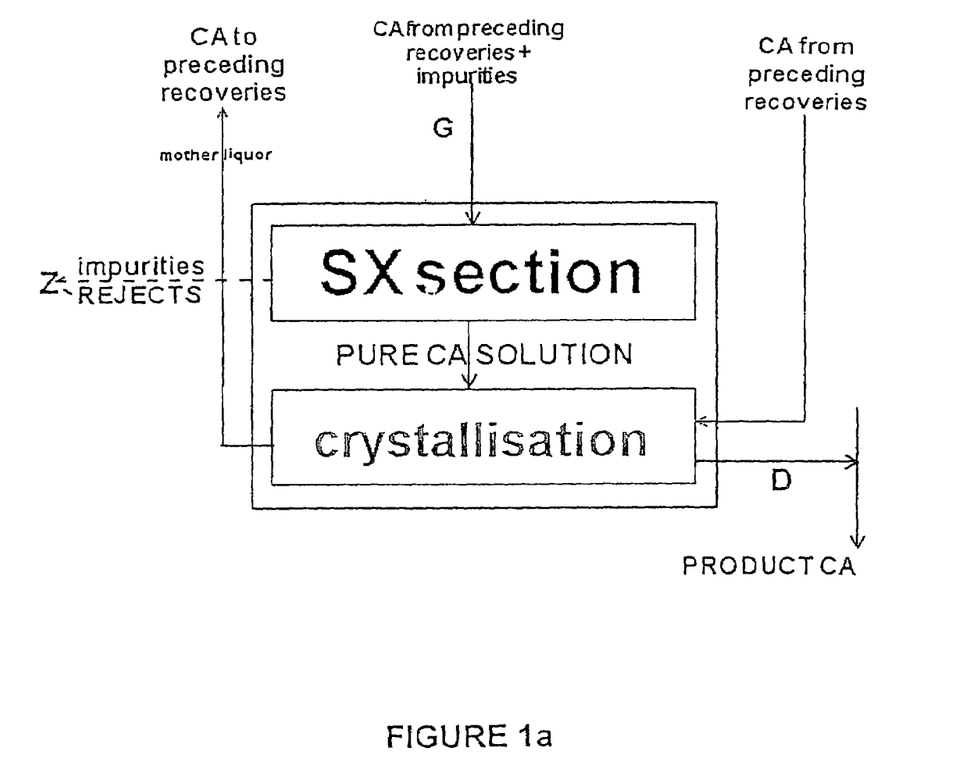
FIG. 1a represents in further detail a feature of FIG. 1.

Two) The primary feed to the system (clarified and de-ionized fermentation broth) [A] is treated in one or more recovery units that apply separation technologies which do not involve Amine Extractants, for partial recovery of citric acid [B], [C] without rejection of impurities. These remain with the non-recovered citric acid [G] that is fed to the SX section of the amine recovery as shown in FIG. 1a.

Three) Citric acid recovered prior to Amine Extraction SX may be of commercial purity grade [B] [C], or of a purity grade that is suitable for direct feeding to the crystallization section of the core unit as illustrated by [b] or consist of streams of both of these.

Four) The aqueous waste stream from the Amine Extractant SX section [Z] services the whole system.

Five) Residual impurities that report to the crystallization section of the core unit collect in the mother liquor, which is recycled [a] to recovery units preceding the core unit.

One key advantage of the described multi-recovery systems, as can be easily appreciated, resides in the fact that the application of amine solvent extraction conserves fully its advantages, namely, providing for recovery of citric acid and rejection of neutral impurities—that are practically complete—while processing only part of the citric acid of the primary feed. An associated key advantage resides in that recoveries by other separation processes that precede SX by Amine Extractants can be selected for application in concentration ranges where they are most efficient.

To illustrate the foregoing, a system is considered that applies sequential crystallization to the primary feed [A] prior to SX. Such a system is described in detail in Example 1 and is considered in its essentials in FIG. 2 and FIG. 3. The fermentation broth feed is subjected to evaporation and crystallization in two successive stages. In the $1^{st}$ of these about 20 (to 40) of the 100 citric acid in the primary feed are recovered at product purity as stream [a]. These 20 CA represent 20% of the 100 CA fed to the system but only 20 of the 120 CA (or about 17%) of the combined primary feed that contains 100 CA and the mother liquor recycle [b] that contains 20 CA. Normally only about 10% would be recoverable by crystallization at the required level of purity from the feed as such. However the recycle of mother liquor [b], which is formed after rejection of impurities in the SX section, lowers the level of impurities in the $1^{st}$ crystallization and makes the higher recovery of pure product possible.

Figure 2:
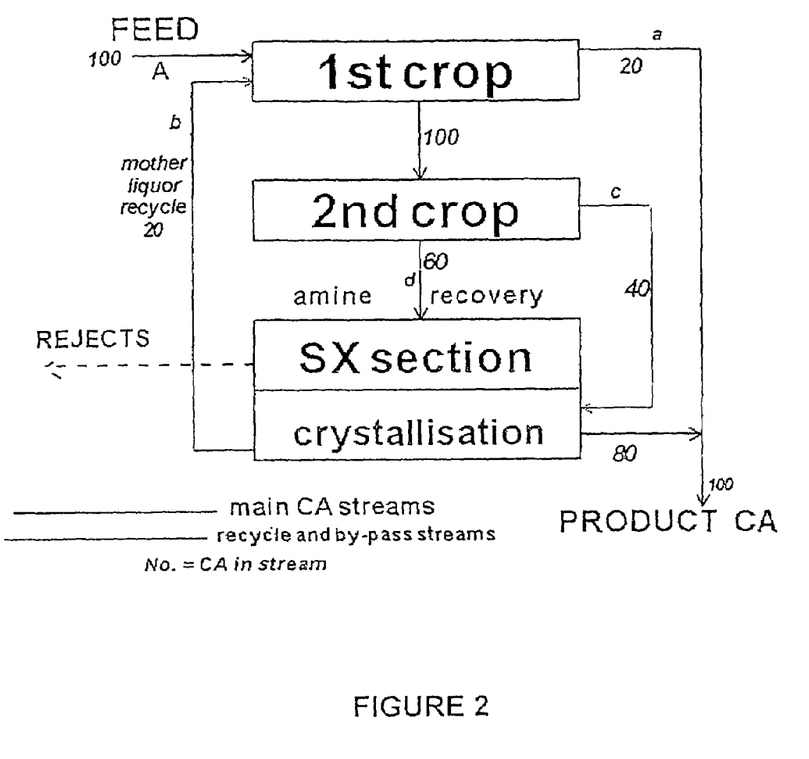
FIG. 2 is a schematic flow sheet representation of a preferred embodiment of the present invention.
Figure 3:
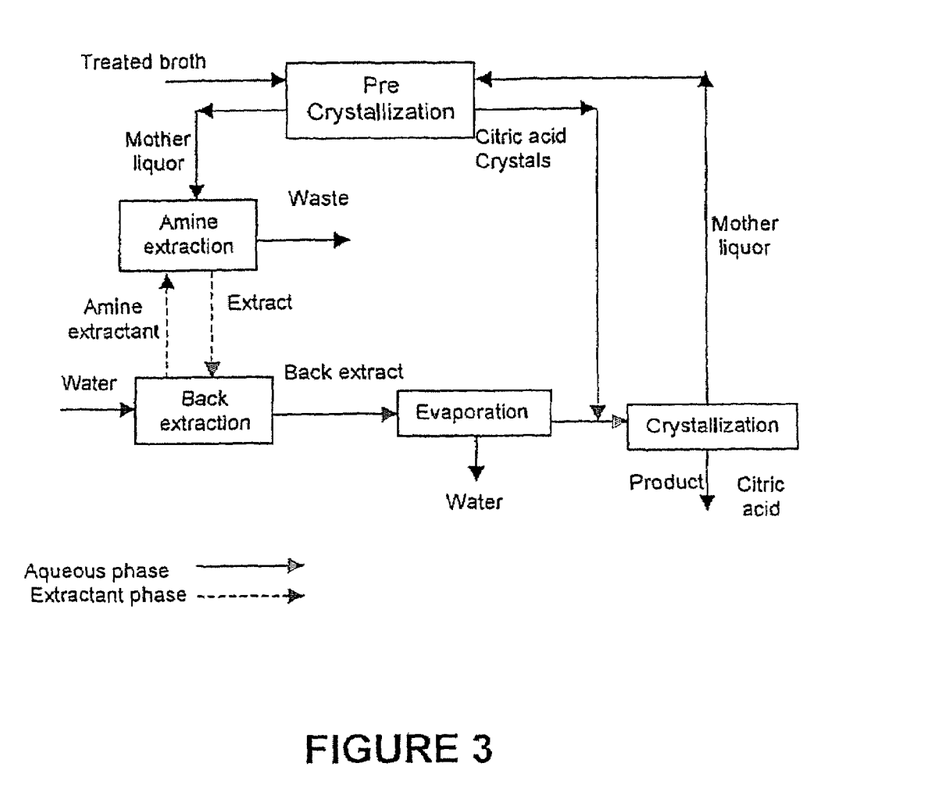
FIG. 3 is a schematic flow sheet representation of a preferred process as described in Example 1 hereinafter.

The crop of the next crystallization [c], which does not have the final level of purity, is still sufficiently pure to be sent directly to the final crystallization, by-passing SX. Thus for 100 units of citric acid fed into the system and recovered at product quality only about 60 go through SX.

Figure 2A:
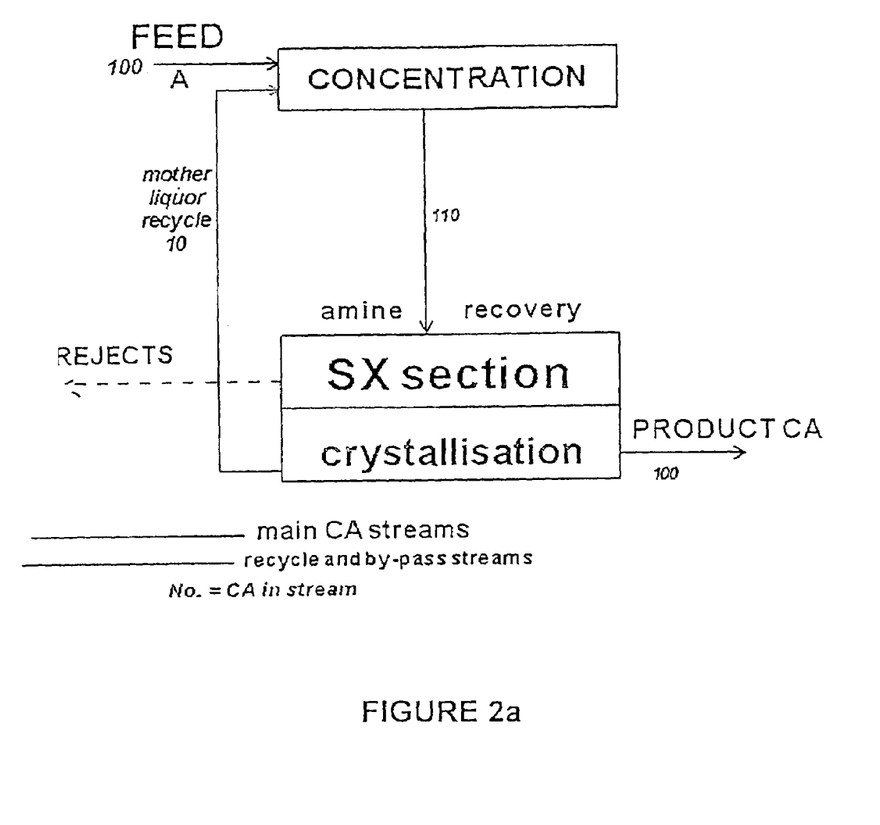
FIG. 2a is a schematic flow sheet representation of a comparable production by present art without the benefit of the present invention.

FIG. 2a represents the equivalent production of 100 CA by conventional amine solvent extraction technology as currently practiced by industry (U.S. Pat. No. 4,275,234) in the same summary fashion. While it obviously entails fewer operations, the SX section required is nearly double in capacity requirements making the whole system materially more expensive in investment and in operating costs. It will be also obvious to a practitioner that the novel system illustrated by FIG. 2 also provides for an efficient, low-cost expansion of an existing plant by as much as 60%.

The concept underlying the invention teaches the provision of one or two successive recovery operations in each of which a fraction of the incoming citric acid is obtained at a high level of purity while substantially all the incoming impurities remain in the fraction that proceeds to the next operation, with amine solvent extraction as the final recovery operation securing the rejection of all impurities. It is a fact of all separation processes that the costs of recovery of a component from a mixture increase steeply at some point with the extent of recovery. Under the invention, separation processes applied in each recovery, having been selected for suitability, can be further optimized by adjusting the extent of recovery and the number of steps adopted—as extensively illustrated in Examples.

The invention does not mandate the choice of particular separation technologies for the recovery or recoveries that precede amine solvent extraction. The actual choice may be affected i.a. by considerations particular to a plant or a location. The two technologies chosen for the purpose of illustrating the practice of the invention are crystallization (referred to herein as CRYS) and extraction by alkanol. The latter (referred to herein as EXAL) is a particular category of extraction by oxygenated solvents mentioned above that is described in detail in Examples below. These technologies provide for four reference modalities of practicing the invention as tabulated below:

|  | Modality | | | |
|---|---|---|---|---|
|  | 1 | 2 | 3 | 4 |
| 1st recovery | CRYS | EXAL | CRYS | EXAL |
| 2ND recovery | None | None | EXAL | CRYS |

Each of these modalities admits variations that further provide for efficiency.

As mentioned previously the invention provides for low-cost expansion of an existing amine solvent recovery plant by adopting it as the core operation in the present invention and adding to it a recovery unit or two recovery units that apply selected separation technologies. Expansion can be effected stage-wise without restricting its eventual scope. As illustrated in FIG. 2 and in detail in the examples hereinafter), Modality 1 provides for an expansion of about 80%. If Modality 3 is applied, with the 2nd EXAL recovery decreasing further by half the citric acid feed to amine recovery, an increase of capacity of well over 200% is obtained.

Extraction of citric acid by a non-amine solvent

Citric acid can be recovered by direct extraction with a water-immiscible organic extractant followed by water stripping of the resulting extract as described, for example, in U.S. Pat. No. 3,944,606, According to U.S. Pat. No. 4,275,234 a citric acid fermentation broth is extracted with a water-immiscible organic extractant which comprises a solution of at least one secondary or tertiary amine in which the aggregate number of carbon atoms is at least 20 in admixture with hydrocarbon and alcoholathe resulting extract is stripped with water at a temperature which is higher, preferably by at least 20.degree.C. than the broth extraction temperature.

According to U.S. Pat. No. 4,344,095 a citric acid fermentation broth is extracted with a mixture of a water-immiscible amine and a water-immiscible organic acid dissolved in a suitable water-immiscible solvent, and the resulting extract is back-extracted with water.

Laboratory results concerning extraction of citric acid by solvents, done in Tate and Lyle laboratories are presented in the following tables and figures.

The distribution of citric acid between water and alkanols is presented in Experiments 1-3.

EXAMPLE 1

The distribution of Citric Acid Between Butanol and Aqueous Solution

Citric acid, Butanol and water at various ratios were added into vials. The vials were shaken at 30° C. The composition of the two resulting phases is presented in Table 1.

TABLE 1

The distribution of citric acid between butanol and aqueous solution

| Butanolic phase | | | Aqueous phase | | | |
|---|---|---|---|---|---|---|
| Citric eq/kg | Citric Wt % | gr Citric/ gr solvent | Citric Eq/kg | Citric Wt % | gr Citric/ gr solvent | Distribution coefficient |
| 0.06 | 0.4 | 0.4 | 0.19 | 1.2 | 1.2 | 0.31 |
| 0.35 | 2.2 | 2.3 | 0.80 | 5.1 | 5.4 | 0.42 |
| 0.71 | 4.6 | 4.8 | 1.6 | 10.1 | 11 | 0.42 |
| 2.1 | 13.5 | 15.6 | 3.6 | 23.3 | 30 | 0.51 |

TABLE 1-continued

The distribution of citric acid between butanol and aqueous solution

| Butanolic phase | | | Aqueous phase | | | |
|---|---|---|---|---|---|---|
| Citric eq/kg | Citric Wt % | gr Citric/ gr solvent | Citric Eq/kg | Citric Wt % | gr Citric/ gr solvent | Distribution coefficient |

EXAMPLE 2

The Distribution of Citric Acid Between Pentanol and Aqueous Solution

Citric acid, Pentanol and water at various ratios were added into vials. The vials were shaken at 30° C. The composition of the two resulting phases is presented in Table 2.

TABLE 2

The distribution of citric acid between pentanol and aqueous solution

| Pentanolic phase | | | Aqueous phase | | | |
|---|---|---|---|---|---|---|
| Citric eq/kg | Citric Wt % | gr Citric/ gr solvent | Citric eq/kg | Citric Wt % | gr Citric/ gr solvent | Distribution coefficient |
| 0.03 | 0.2 | 0.2 | 0.17 | 1.1 | 1.1 | 0.16 |
| 0.10 | 0.6 | 0.6 | 0.57 | 3.6 | 3.8 | 0.16 |
| 0.48 | 3.0 | 3.1 | 2.4 | 15.2 | 18 | 0.18 |
| 0.95 | 6.1 | 6.5 | 4.1 | 26.0 | 35 | 0.18 |
| 3.4 | 21.5 | 27 | 8.1 | 52.1 | 109 | 0.25 |

EXAMPLE 3

The distribution of Citric Acid Between Hexanol and Aqueous Solution

Citric acid, Hexanol and water at various ratios were added into vials. The vials were shaken at 30° C. The composition of the two resulting phases is presented in Table 3.

TABLE 3

The distribution of citric acid between Hexanol and aqueous solution

| Hexanolic phase | | | Aqueous phase | | | |
|---|---|---|---|---|---|---|
| Citric eq/kg | Citric Wt % | gr Citric/gr solvent | Citric eq/kg | Citric Wt % | gr Citric/ gr solvent | Distribution coefficient |
| 0.05 | 0.4 | 0.4 | 0.58 | 3.7 | 3.8 | 0.09 |
| 0.07 | 0.4 | 0.4 | 0.68 | 4.4 | 4.6 | 0.10 |
| 0.17 | 1.1 | 1.1 | 1.6 | 10.2 | 11.4 | 0.10 |
| 0.62 | 4.0 | 4.1 | 4.5 | 28.6 | 40 | 0.10 |
| 2.1 | 13.5 | 15.7 | 8.5 | 54.1 | 118 | 0.13 |

In solutions containing both glucose and citric acid, citric acid is selectively extracted into the NA solvent. The citric/glucose selectivity decreases with the increase in the distribution of citric into the solvent phase.

Although, non-amine solvents can efficiently extract citric acid, the results indicate that the efficiency of the extraction is reduced at lower citric acid concentrations thus, high extraction yields require large number of extraction stages.

The distribution of citric acid by an amine extractant follows a different pattern. The distribution coefficient at high citric acid concentrations is much lower that at lower citric acid concentration example of this phenomenon is presented in Experiment 4.

EXAMPLE 4

The Distribution of Citric Acid between Amine Extractant and Aqueous Solution Citric acid, Amine extractant and water at various ratios were added into vials. The vials were shaken at 30° C. The composition of the two resulting phases is presented in Table 4

TABLE 4

The distribution of citric acid between an amine extractant and aqueous solution at 50° C.

| Amine phase | | | Aqueous phase | | | |
| --- | --- | --- | --- | --- | --- | --- |
| Citric eq/kg | Citric Wt % | Gr Citric/ gr solvent | Citric eq/kg | Citric Wt % | gr Citric/ gr solvent | Distribution coefficient |
| 0.09 | 0.6 | 0.6 | 0.08 | 0.5 | 0.5 | 1.21 |
| 0.15 | 0.9 | 1.0 | 0.14 | 0.9 | 0.9 | 1.05 |
| 0.46 | 3.0 | 3.1 | 0.41 | 2.6 | 2.7 | 1.15 |
| 0.87 | 5.6 | 5.9 | 0.74 | 4.7 | 5.0 | 1.19 |
| 1.43 | 9.2 | 10.1 | 1.64 | 10.5 | 11.7 | 0.86 |
| 1.84 | 11.8 | 13.3 | 3.71 | 23.7 | 31 | 0.43 |
| 1.96 | 12.5 | 14.3 | 4.75 | 30.4 | 44 | 0.33 |
| 2.1 | 13.3 | 15.4 | 6.4 | 41.0 | 70 | 0.22 |
| 2.3 | 14.7 | 17.3 | 8.2 | 52.3 | 110 | 0.16 |

The amine extractant is composed of alamine 47% A304, 3% octanol in isopar.K. (Alamine 336 is a long chained tertiary amine, Isopark is a commercially diluent consisting of high boiling point carbohydrate).

The above data indicate that amine extractant is very efficient in the extraction at low citric acid concentrations while the non amine extractant is more efficient at the higher citric acid concentrations, thus suggesting that the combination of the two extraction method will be efficient.

EXAMPLE 4

Pre Crystallization, Amine Extraction and Re Crystallization

The procedure was according to the following steps, which should be read in conjunction with FIG. 3.

One) 66 g of treated broth, containing 27.6 g citric acid and 2 g impurities and 4.44 g mother liquor (obtained as a bleed from mother liquor from crystallization of relatively pure citric acid solution in stage d) were evaporated under vacuum at 70° C. in a crystallizer. 11.44 g of 96.1 wt % citric acid wet solids and 17.25 g of mother liquor were obtained. The mother liquor contained 10.12 g citric acid and 1.96 g impurities.

Two) 17.25 g mother liquor solution obtained in a). was extracted at 40° C. in five counter-current stages (simulated by five separatory funnels) with 52.7 g of recycled extractant containing 47% w/w Alamine 336, 50% w/w IsoparK (mixture of high boiling point hydrocarbons produced by), 3% w/w of 1-n-octanol.

Three) 62.75 g Extract containing 16% w/w of citric acid was stripped at 100° C. in five simulated counter-current stages with 22.3 g of H$_2$O to yield 32.3 g of an aqueous back-extract containing 31% w/w citric acid and less than 0.1% impurities. At the same time 52.7 g of extractant phase practically free of CA was obtained which was ready for recycle to a). after cooling.

Four) 32.3 g of back extract obtained in c) was evaporated under vacuum at 70° C. to form a solution containing 50% w/w of citric acid. 11.4 g of citric acid crystals obtained in a) were dissolved in the concentrated solution and the solution was crystallized to give 27.6 g of citric acid crystals (>99.8% w/w CA) and mother liquor. The mother liquor is ready to be recycled to a).

EXAMPLE 5

Non Amine (NA) Solvent Extraction, Amine Extraction and Re Crystallization

Figure 4:
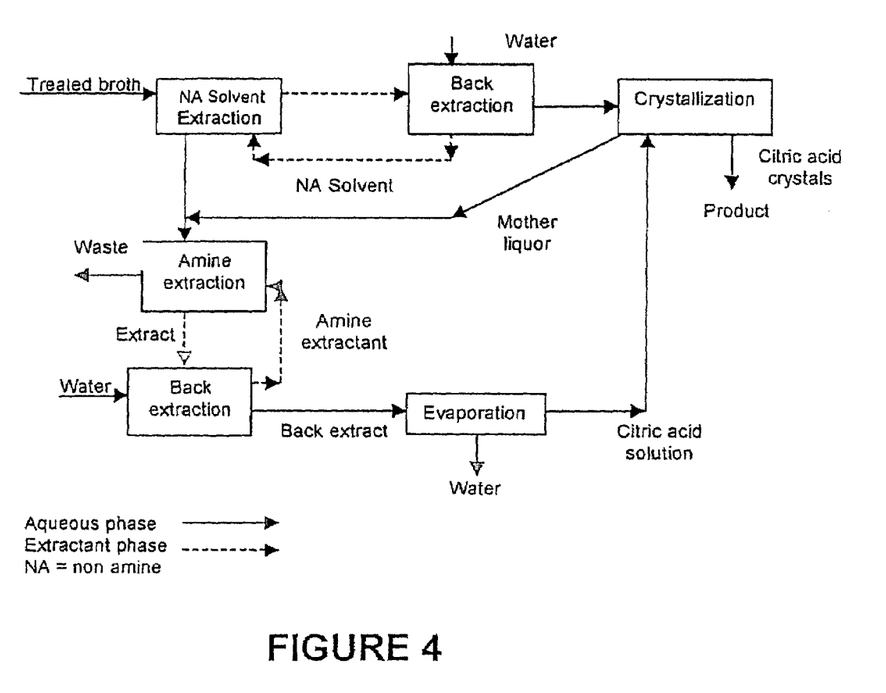
FIG. 4 is a schematic flow sheet representation of a preferred process as described in Example 2 hereinafter.

The procedure was according to the following steps that should be read in conjunction with FIG. 4 appended hereto:

One) 46.2 g of 58% w/w citric acid treated broth was extracted at 40° C. in four counter-current stages (simulated by four separatory funnels) with 158.3 g of recycled extractant composed of 154.6 g hexanol and 3.7 g citric acid. The resulting phases were: about 180 gr extractant containing 13.8% w/w citric acid and 0.148% w/w of impurities and 26.6 g raffinate containing 24.8% w/w citric acid and 6.5% w/w impurities.

Two) 180 g extract containing 17.8% w/w of citric acid was stripped 40° C. in four simulated counter-current stages with 20.7 g of H$_2$O to yield 42.5 g of an aqueous back-extract containing 50% w/w of citric acid. The total solutes contain about 99% w/w of citric acid. At the same time 158.3 g of extractant phase containing 3.7 g of citric acid was obtained which was ready for recycle to Stage a).

Three) 42.5 g of a 50% w/w back extract obtained in b) were evaporated under vacuum at 70° C. 39.5 g Back extract obtained in the amine extraction stages (Stages d) and the concentrated solution obtained in the NA extraction were crystallized to give 27.45 g of citric acid crystals (99.8% w/w CA) and mother liquor.

Four) 42 g solution were obtained by mixing the mother liquor obtained in c) with the raffinate obtained in b). The solution contained 32.9% w/w citric acid and 6.0% w/w impurities. The solution was extracted at 40° C. in five counter-current stages (simulated by five separatory funnels) with 63.5 g of recycled extractant containing 47% w/w Alamine 336, 50% w/w IsoparK, 3% w/w of 1-n-octanol. 47.5 g extract containing 18% w/w of citric acid was stripped at 40° C. in five simulated counter-current stages with 18 g of H$_2$O to yield 38.9 g of an aqueous back-extract containing 36.6% w/w of 99% wt/wt citric acid. At the same time 47.5 g of extractant phase practically free of CA was obtained which was ready for recycle after cooling. The back extract obtained in c) was evaporated under vacuum at 70° C. to form a solution containing 50% w/w of citric acid were ready to be added to the crystallizer.

EXAMPLE 6

Figure 5:
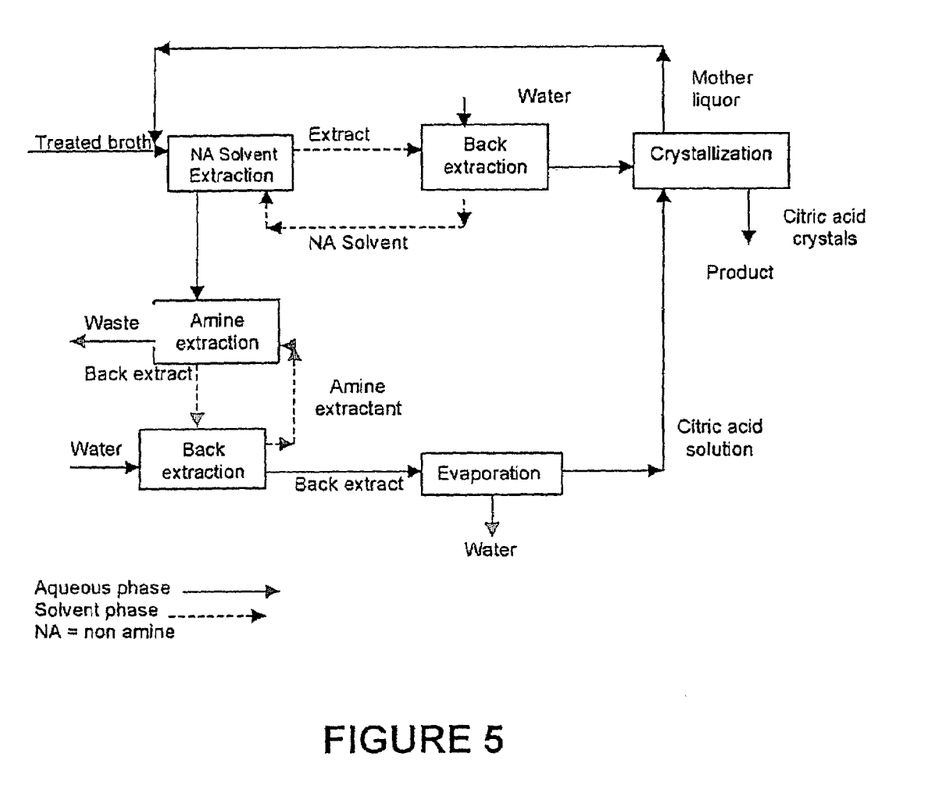
FIG. 5 is a schematic flow sheet representation of a preferred process as described in Example 3 hereinafter.

Non Amine (NA) Solvent Extraction, Amine Extraction and Re Crystallization. Recycle of the Mother Liquor to the NA Solvent Extraction The procedure was according to the following steps that should be read in conjunction with FIG. 5 appended hereto:

One) 46.2 g of 58% w/w citric acid treated broth and 3.1 g mother liquor from the crystallizer were mixed and were extracted at 40° C., in four counter-current stages (simulated by four separatory funnels), with 177.7 g of recycled extractant composed of 177.7 g hexanol and 3.75 g citric acid. The resulting phases were: about 207 gr extractant containing 13.8% w/w citric acid and 0.16% w/w of impurities and 26 g raffinate containing 21.5% w/w ca and 7.4% w/w impurities.

Two) 206.5 g extract containing 113.8% w/w of citric acid was stripped at 40° C. in four simulated counter-current stages with 20.5 g of $H_2O$ to yield 50 g of an aqueous back-extract containing 50% w/w of citric acid. The total solutes contain about 98.6% wt/wt of citric acid. At the same time 181.9 of extractant phase containing 3.75 g of citric acid was obtained which was ready for recycle to a).

Three) 48 g of a 50% w/w back extract obtained in b) were evaporated under vacuum at 70° C. 30 g Back extract obtained in the amine extraction stages (Stages d) and the concentrated solution obtained in the NA extraction were crystallized to give 26.8 g of citric acid crystals (99.8% w/w CA) and mother liquor.

Four) The raffinate from Stage a) was extracted at 40° C. in five counter-current stages (simulated by five separatory funnels) with 33.5 g of recycled extractant containing 47% w/w Alamine 336, 50% w/w Isopark., 3% w/w of 1-n-octanol. 38.8 g extract containing 14.2% w/w of citric acid was stripped at 100° C. in five simulated counter-current stages with 25 g of $H_2O$ to yield 25 g of an aqueous back-extract containing 18% w/w of 98.6% w/w citric acid. At the same time 33.3 g of extractant phase practically free of CA was obtained which was ready for recycle after cooling. The back extract was evaporated under vacuum at 70° C. to form a solution containing 50% w/w of citric acid was ready to be added to the crystallizer (c).

EXAMPLE 7

Figure 6:
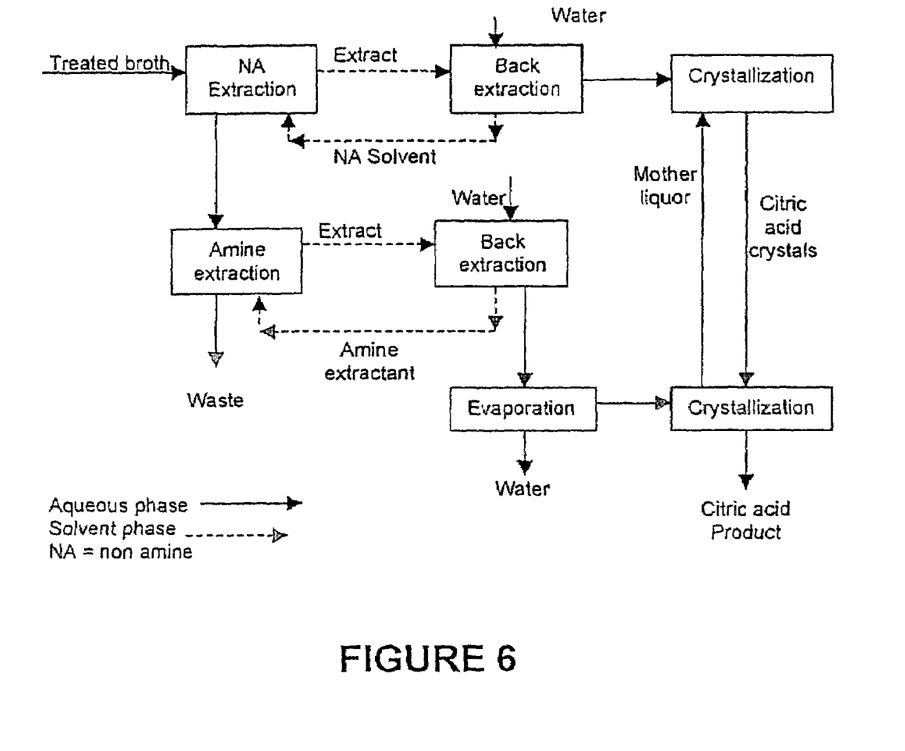

Solvent Extraction+Crystallization, Amine Extraction and Recrystallization. Back Extraction with Water The procedure was according to the following steps that should be read in conjunction with FIG. 6 appended hereto:

One) 50 gr of 60% w/w citric acid treated broth were extracted at 40° C. in four counter-current stages (simulated by four separatory funnels) with 158.3 g of recycled extractant composed of 154.6 gr hexanol and 3.7 g citric acid. The resulting phases were: about 180 gr extractant containing 13.8% w/w citric acid and 0.148% w/w of impurities and 26.6 gr raffinate containing 24.8% w/w citric acid and 6.5% w/wt impurities.

Two) 180 gr extract containing 17.8% w/w of citric acid was stripped at 40° C. in four simulated counter-current stages with 24.8 g of $H_2O$ to yield 42.5 g of an aqueous back-extract containing 50% w/w of citric acid. The total solutes contain about 99% w/w of citric acid. At the same time 158.3 g of extractant phase containing 3.7 g of citric acid was obtained which was ready for recycle.

Three) 42.5 g of a 50% w/w back extract obtained in b) were evaporated under vacuum at 70° C. The concentrated solution was crystallized to give 19 g of citric acid crystals (99.8% w/w CA) and mother liquor.

Four) 29.6 g solution obtained by mixing the mother liquor obtained in c) with the raffinate obtained in b). The solution contained 29.7%-wt/wt CA and 6.6% w/w impurities. The solution was extracted at 40° C. in five counter-current stages (simulated by five separatory funnels) with 51.4 g of recycled extractant containing 47% w/w Alamine 336, 50% w/w IsoparK., 3% w/w of 1-n-octanol. 59.9 g extract containing 14.2% w/w of citric acid was stripped at 100° C. in five simulated counter-current stages with 30.3 g of $H_2O$ to yield 38.9 g of an aqueous back-extract containing 28% w/w of 99% w/w citric acid. At the same time 51.4 g of extractant phase practically free of CA was obtained which was ready for recycle after cooling.

Five) 38.9 g of back extract obtained in 4.4 were evaporated under vacuum at 70° C. to form a solution containing 45% w/w of citric acid. 19 g of citric acid crystals obtained in c) were dissolved in the concentrated and the solution was crystallized to give 22.9 g of citric acid crystals (>99.9% w/w CA) and mother liquor.

EXAMPLE 8

Figure 7:
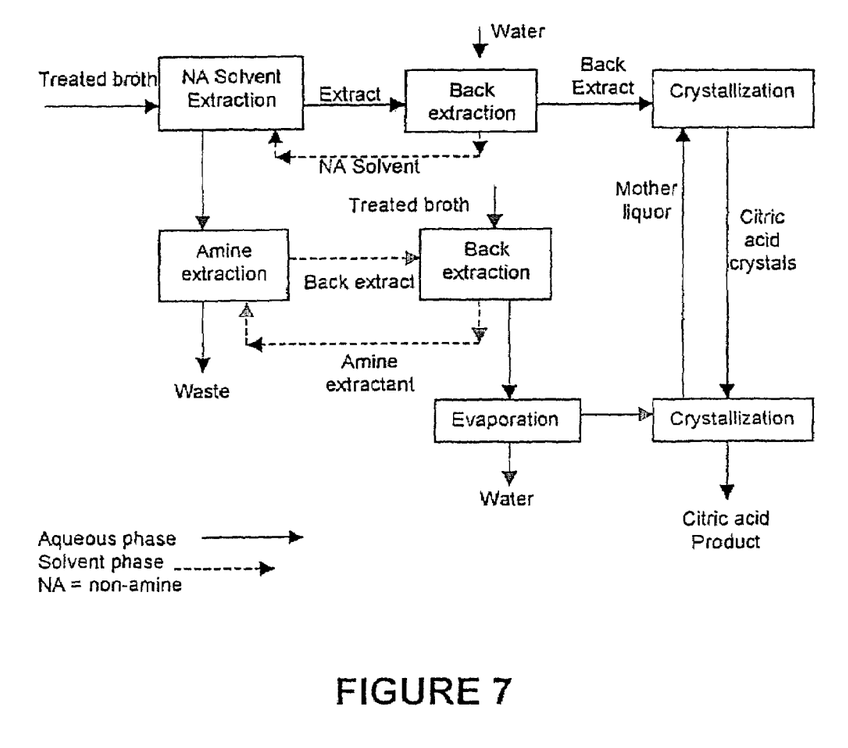
FIG. 7 is a schematic flow sheet representation of a preferred process as described in Example 5 hereinafter.

Solvent Extraction+Crystallization, Amine Extraction and Re Crystallization. Back Extraction with Treated Broth The procedure was according to the following steps that should be read in conjunction with FIG. 7 appended hereto:

One) The procedure was similar to that in Example 4.

Two) 180 g extract containing 17.8% w/w of citric acid was stripped at 40° C. in four simulated counter-current stages with 24.8 g of $H_2O$ to yield 42.5 g of an aqueous back-extract containing 50% w/w of citric acid. The total solutes contain about 99% wt/wt of citric acid. At the same time 158.3 g of extractant phase containing 3.7 g of citric acid was obtained which was ready for recycle.

Three) 42.5 g of a 50% w/w back extract obtained in 5.2 were evaporated under vacuum at 70° C. The concentrated solution was crystallized to give 19 g of citric acid crystals (99.8% w/w CA) and mother liquor.

Four) 29.6 g solution obtained by mixing the mother liquor obtained in 5.3 with the raffinate obtained in 5.2. The solution contained 29.7% w/w CA and 6.6% w/w impurities. The solution was extracted at 40° C. in five counter-current stages (simulated by five separatory funnels) with 51.4 g of recycled extractant containing 47% w/w Alamine 336, 50% w/w Isopark, 3% w/w of 1-n-octanol. 59.9 g extract containing 14.2% w/w of citric acid was stripped at 100° C. in five simulated counter-current stages with 30.3 g of $H_2O$ to yield 38.9 g of an aqueous back-extract containing 28% w/w of 99% w/w citric acid. At the same time 51.4 g of extractant phase practically free of CA was obtained which was ready for recycle after cooling.

Five) 38.9 g of back extract obtained in d) were evaporated under vacuum at 70° C. to form a solution containing 45% w/w of citric acid. 19 g of citric acid crystals obtained in c) were dissolved in the concentrated and the solution was crystallized to give 22.9 g of citric acid crystals (>99.9% w/w CA) and mother liquor.

In all cases

1. Back extraction for the extraction with amine exractant or with NA extractant can be done with water, decationized beer or concentrated decationized beer, mother liquor from any crystallizer or solutions obtained by dissolution of citric acid crystals.

2. Mother liquor from any crystallization stage could be recycled to another crystallization stage (of lower purity or to any of the extraction units used in the process.

3. Mother liquor from any crystallization stage could be recycled to any extraction stage.

4. The no-amine extraction product may by crystallized in a separate crystallization unit or be added to the SX section crystallization unit 5. Back extraction in SX or non-amine extraction may be fed by water or/and citric acid solution from various process stages.
6. Addition of the citric acid solution can be done to the first extraction stage (extractant exiting stage or to any intermediate extraction stage. The same can be said for the solution used for back extraction.
7. The fermentation broth can be subjected to any pre treatment stages including ultra filtration, decationization, active carbon treatment, pre extraction by solvent or resin to remove impurity acids and any other treatment used in the field.

It will be evident to those skilled in the art that the invention is not limited to the details of the foregoing illustrative embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A process for the recovery of citric acid from an aqueous solution feed stream originating in fermentation of carbohydrates and utilizing an amine solvent extraction step for separation of impurities comprising:
    a) subjecting said aqueous solution feed stream A to a treatment for partial recovery of citric acid, wherein said treatment is other than amine solvent extraction, to form a first portion of purified citric acid B and a secondary feed stream F;
    b) subjecting at least a portion G of said secondary feed stream F to a treatment consisting of amine solvent extraction to form a second portion of purified citric acid solution and to reject substantial of impurities initially present in said portion of said secondary feed stream
    c) subjecting said second portion of purified citric acid solution to crystallization; and
    d) recycling mother liquor from said crystallization to step a).

2. A process according to claim 1 wherein the treatment step a) is a multi-step treatment.

3. A process according to claim 1 wherein the treatment step a) is crystallization.

4. A process according to claim 2 wherein the multi-steps of said multi-step treatment are crystallization and recrystallization.

5. A process according to claim 1 wherein the treatment step a) is non-amine extraction.

6. A process according to claim 2 wherein the multi-steps of said multi-step treatment are non-amine extraction followed by crystallization.

7. A process according to claim 2 wherein the multi-steps of said multi-step treatment are crystallization followed by non-amine extraction.

8. A process according to claim 1 wherein the initial secondary feed stream F formed in step a, prior to being sent to said treatment of amine solvent extraction, is subjected to a second step of partial citric acid recovery to form a partially purified citric acid C and a tertiary feed stream G wherein said tertiary feed stream is subjected to a treatment consisting of amine solvent extraction according to step b and said partially purified citric acid bypasses step b and is directly subjected to crystallization treatment together with the purified citric acid solution b produced in step b.

9. A process according to claim 1 wherein said aqueous solution feed stream A contains citric acid at a concentration of between about 16% and 75%.

10. A process according to claim 1 wherein said secondary feed stream F contains citric acid at a concentration of about 5% to 30%.

11. A process according to claim 1 wherein said secondary feed stream F contains citric acid at a concentration of about 16% to 75%.

* * * * *